United States Patent [19]

Inai

[11] Patent Number: 5,590,652
[45] Date of Patent: Jan. 7, 1997

[54] DRIVE CIRCUIT FOR LIGHT-EMITTING DIODE IN PULSE OXIMETER

[75] Inventor: Takashi Inai, Tokyo, Japan

[73] Assignee: Nihon Kohden Corporation, Tokyo, Japan

[21] Appl. No.: 605,583

[22] Filed: Feb. 22, 1996

Related U.S. Application Data

[63] Continuation of Ser. No. 76,746, Jun. 15, 1993, abandoned.

[30] Foreign Application Priority Data

Jun. 15, 1992 [JP] Japan .................... 4-154805
Jun. 7, 1993 [JP] Japan .................... 5-135739

[51] Int. Cl.$^6$ .................................................. A61B 5/00
[52] U.S. Cl. ........................ 128/633; 128/666; 356/41
[58] Field of Search .................... 128/633–4, 664–6; 356/41

[56] References Cited

U.S. PATENT DOCUMENTS

| | | | |
|---|---|---|---|
| 4,603,700 | 8/1986 | Nichols et al. | 128/665 |
| 4,807,630 | 2/1989 | Malinouskas | 128/666 |
| 5,040,538 | 8/1991 | Mortazavi | 128/633 |
| 5,193,543 | 3/1993 | Yelderman | 128/633 |

*Primary Examiner*—Angela D. Sykes
*Assistant Examiner*—Robert L. Nasser, Jr.
*Attorney, Agent, or Firm*—Sughrue, Mion, Zinn, Macpeak & Seas

[57] ABSTRACT

Disclosed is a drive circuit for driving a light emitting diode in a pulse oximeter comprising at least two light emitting elements different in wavelength for irradiating a living tissue containing an arterial blood; a light receiving element for receiving light containing one of a reflected light and a transmitted light irradiated from the light emitting elements; a power supply for applying intermittently an inverse bias voltage toward the light emitting elements; and an inductor for applying an inverse electromotive voltage to the light emitting elements, the inductor being connected to the light emitting elements in parallel, wherein a ratio between light absorption change with respect to two wavelengths obtained from optical outputs of the light receiving element so as to obtain a degree of oxygen saturation of arterial blood.

31 Claims, 5 Drawing Sheets

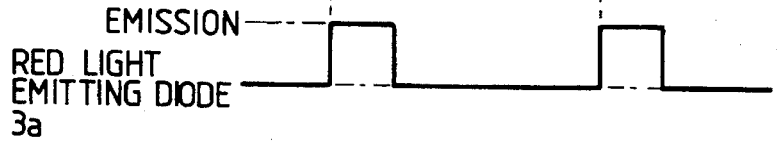
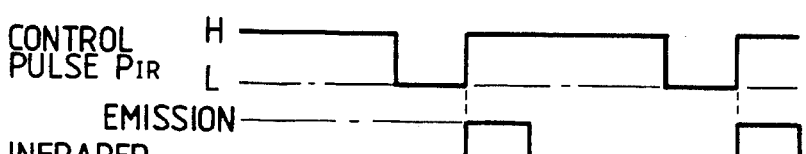
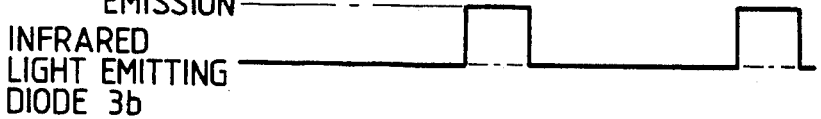
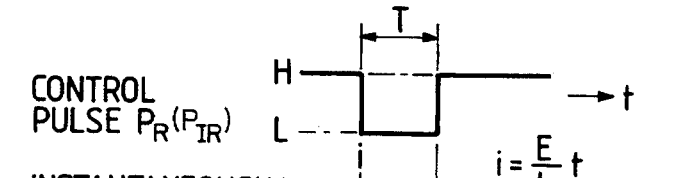
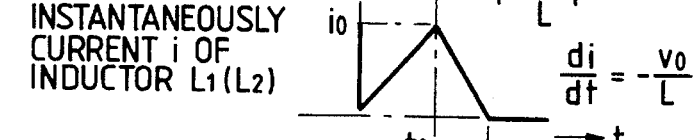
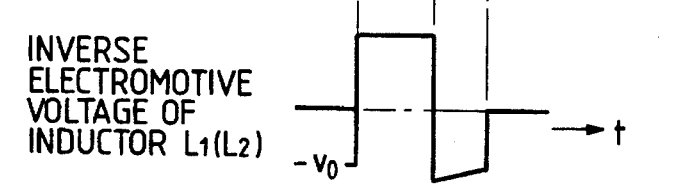

FIG. 8
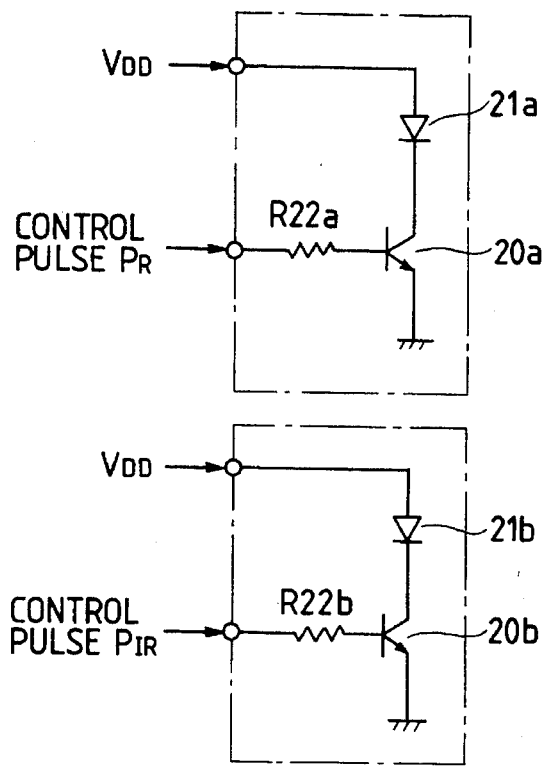
FIG. 9(a) CONTROL PULSE P_R
FIG. 9(b) EMISSION LIGHT EMITTING DIODE 21a
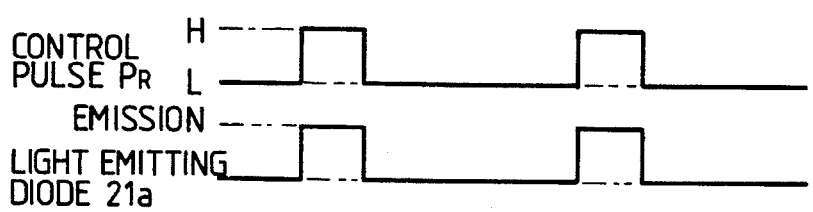
FIG. 9(c) CONTROL PULSE P_IR
FIG. 9(d) EMISSION LIGHT EMITTING DIODE 21b
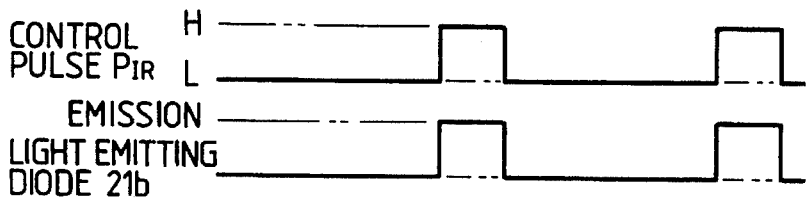

DRIVE CIRCUIT FOR LIGHT-EMITTING DIODE IN PULSE OXIMETER

This is a continuation of application Ser. No. 08/076,746 filed Jun. 15, 1993, now abandoned.

BACKGROUND OF THE INVENTION

1. Field of the Invention

This invention relates to a pulse oximeter for continuously measuring a degree of oxygen saturation of arterial blood of living tissue by light emitting and receiving elements in non-invasive condition, more specifically, relates to a drive circuit, used for the pulse oximeter, for driving two light beams emitting elements to transmit two light having different in wavelength to the living tissue.

2. Prior Art

In the conventional art, a pulse oximeter is used for measuring an oxygen saturation of arterial blood in non-invasive condition. This type of the pulse oximeter operates to measure the oxygen saturation as follows. Red and infrared light different in wavelength have been irradiated to an object and the oxygen saturation is continuously measured in non-invasive condition on the basis of ratio of change of the light absorption of two light beams.

This measurement is performed by fitting a probe to finger or an earlobe. The probe is provided with two light emitting elements (such as light emitting diode) for irradiating red and infrared light different in wavelength and a light receiving element (photodiode or the like) for outputting a photoelectric transfer signal in accordance with a light receiving level of a reflected light or a transmitted light of two light emitting elements, respectively. For example, a wavelength ($\lambda$) of 660 nm is used for the red light and a wavelength ($\lambda$) of 940 nm is used for the infrared light. The two light beams are irradiated to the living tissue on a time sharing basis.

After that, a degree S of the oxygen saturation is measured from a ratio of a light absorption change which is calculated on the basis of the photoelectric transfer signal relating to each wavelength. The ratio $\phi$ between the light absorption of the two different wavelengths and the degree S of the oxygen saturation are expressed by the following equation (1) and (2), respectively:

$$\phi = \Delta A1 / \Delta A2 \quad (1)$$

A1: light absorption change of wavelength of red light
A2: light absorption change of wavelength of infrared light $$S = f(\phi) \quad (2)$$

f: function of ratio $\phi$ between light absorption between two wavelengths.

Next, a drive circuit for driving two light-emitting diodes on the time sharing basis is described hereinafter.

FIG. 8 is showing a circuit diagram indicating conventional drive circuit for driving the light emitting element on the pulse oximeter. As shown in FIG. 8, a red and an infrared light emitting diodes are driven by two independent drive circuits, respectively. This drive circuit corresponds to a transistor switching circuit as generally used. A light emitting diode 21a for emitting a red light is connected in a forward direction between the collector of switching transistor 20a and a supply end of the direct current voltage supply VDD. An emitter of a switching transistor 20b is grounded and a base of the switching transistor 20b is connected in series to a resister R22a for inputting a control pulse PR therein.

A light emitting diode 21b for emitting an infrared light is connected in a forward direction between the collector of switching transistor 20b and a supply end of the direct current voltage supply VDD. An emitter of a switching transistor 20b is grounded and a base of the switching transistor 20b is connected in series to a resister R22b for inputting a control pulse PR therein.

Next the operation of the conventional drive circuit is described hereinafter.

FIG. 9 is a timing chart showing a light emission timing of each light emitting diode operated by a control pulse. Control pulses PR and PR shown in FIGS. (a) and (c), respectively, are changed to a high level (H) or a low level (L) for irradiating the light emitting diode on the time basis. Namely, when the control pulse PR is in the high level, the switching transistor 20a turns on (conducting) so that the light emitting diode 21a is irradiated as shown in FIG. 9(b) and when the control pulse PR is in the low level, the switching transistor 20a turns off (non-conducting) so that light emitting diode 21a is in non-light emission condition.

On the other hand, as shown in FIG. 9(d), when the control pulse PIR is in the high level (H), the switching transistor 20b turns on so that the light emitting diode 21b is irradiated. Further, the control pulse PIR is in the low level (L) so that the switching transistor 20b turns off so that the light emitting diode 21b is in non-irradiative condition. In this case, the two light emitting diodes are alternatively irradiated with a light emission ratio being not more than 50%.

In the conventional device, the starting emission voltage for the light emitting diode is about 2 V. However, it is necessary to apply a high voltage (DC power supply VDD) to the switching transistor in the consideration of a variation of the forward direction characteristic of the light emitting diode and a voltage drop occurred by an internal resistance when the switching transistor 20 turns on. Therefore, the conventional device employs a power supply circuit for converting a commercial AC power supply to DC power.

In the conventional drive circuit for driving the light emitting diode in the pulse oximeter, when the high voltage (DC voltage VDD) is applied to the switching transistor in consideration of the variation of the forward direction characteristic of the light emitting diode and the voltage drop occurred by the internal resistance when the switching transistor 20 turns on, a power supply utilization efficiency is insufficient.

For example, when DC voltage 9 V is applied to an anode of the light emitting diode, a cathode voltage thereof is in approximately 7 V when the light emitting diode is irradiated. Assuming that a current flowing to the light emitting diode considers i, a total power consumption becomes 9×i (W). 7×i (W) is consumed from the total power consumption 9×i (W) when the switching transistor turns on. Since a power consumption of the light-emitting diode is 2×i (W), the power utilization efficiency remains at approximately 22% only.

As a result, in the conventional pulse oximeter, notwithstanding it is required to decrease power to be uselessly consumed in the conventional device, it is impossible to decrease the total power consumption.

Although attempts have been made to lower the light emission duty ratio so as to decrease the power consumption, the S/N ratio is reduced. Thus, the measurement of the oxygen saturation may not be performed in accuracy. For the reason described above, there is not provided a portable pulse oximeter which is capable of long measurement with a cell.

SUMMARY OF THE INVENTION

In view of the forgoing problem, an object of the present invention is to provide a drive circuit for driving two light emitting elements in an pulse oximeter on a time sharing basis by utilizing an inverse electromotive voltage of an inductor when a power supply voltage is not more than a light emission starting voltage, to decrease a current consumption without sacrificing the S/N ratio.

According to an aspect of the present invention, there is provided a drive circuit for driving a light emitting diode in a pulse oximeter for obtaining the degree of oxygen saturation of arterial blood by first irradiating a living tissue containing the arterial blood with light different in wavelength for light emitting diodes, and receiving a reflected or transmitted light of the light by a light receiving element, respectively, and obtaining a ratio between light absorption change with respect to two wavelengths from optical outputs of the light receiving element so as to obtain a degree of oxygen saturation of arterial blood, the drive circuit comprises: power supply for intermittently supplying an inverse bias voltage to the light emitting elements and an inductor for supplying an inverted voltage to the light emitting elements, the inductor connected to the light emitting element in parallel.

According to the present invention, the power supply includes a DC power supply and switching means for switching an application of an output voltage of the DC power supply to the light emitting elements connected in parallel and the inductor.

According to the present invention, the power supply further includes voltage changing means for gradually increasing the output voltage of the DC power supply applied to the light emitting elements connected in parallel and the inductor from 0 volts.

According to the present invention, the drive circuit includes a pulse generator, a semiconductor element connected to an output of the pulse generator in a forward direction, one light emitting element with one wavelength being connected in parallel to the other emitting element and an inductor, which receives a pulse signal generated by the pulse generator, a delay circuit for delaying a pulse signal generated from the semiconductor element, the other light emitting element with the other wavelength being connected in parallel to one emitting element and an inductor, which receive a pulse signal passing through the delay circuit.

According to the present invention, the power supply of the drive circuit includes a sawtooth waveform generator, a semiconductor element connected to an output of the sawtooth waveform circuit in a forward direction, wherein said power supply operates to supply a sawtooth wave passing through the semiconductor element to the light emitting elements connected in parallel and an inductor.

According to the present invention, the power supply includes a sawtooth waveform generator, a semiconductor element connected to an output of the sawtooth waveform generator in a forward direction, one light emitting element with one wavelength connected to the other light emitting element in parallel and an inductor which receive a sawtooth wave passing through the semiconductor element and a delay circuit for delaying sawtooth wave passing through the semiconductor element, the other light emitting element connected to one light emitting element in parallel and inductor, which receive the sawtooth waveform passing through the delay circuit.

According to the present invention, the drive circuit includes switching means for alternatively emitting two light emitting elements different in wavelength by utilizing one inductor.

According to the present invention, a drive circuit for a light-emitting diode in a pulse oximeter is arranged so that two light emitting elements for emitting light different in wavelength are alternately irradiated to a living tissue including an arterial blood, one wavelength is used for the red light and the other wavelength is used for the infrared light.

With the arrangement stated above, according to the drive circuit for a light emitting diode in a pulse oximeter, the light emitting diode is irradiated by utilizing the inverse voltage generated by the inductor. Moreover, it is capable of alternatively irradiating two light emitting elements by utilizing the inverse voltage generated by one inductor. Therefore, since the circuit is simplified, when the voltage is not more than the light emission starting voltage of the light emitting element, two light emitting elements could be alternatively irradiated by utilizing the inverse voltage generated by one inductor so as to decrease a current consumption without sacrificing the S/N ratio. Therefore, the present invention leads the development of a pulse oximeter utilizes a battery such as a relative low voltage with long time measurment.

BRIEF DESCRIPTION OF THE DRAWINGS

FIGS. 2(a)–2(d) is a timing chart of a light emission timing of a red light emitting diode and an infrared light emitting diode in response to control pulses according to the present invention, respectively.

FIG. 3 is a timing chart showing a relationship between the control pulse and a current and an inverse voltage of an inductor according to the present invention;

FIG. 8 is a circuit diagram of a conventional pulse oximeter using drive circuts for light emitting diodes; and FIG. 9(a) to (d) are timing chart of a light emission timing of light emitting diodes in the conventional pulse oximeter.

DETAILED DESCRIPTION OF THE PREFERRED EMBODIMENTS

Preferred embodiments will now be described in reference with accompanying drawings.

Figure 1:
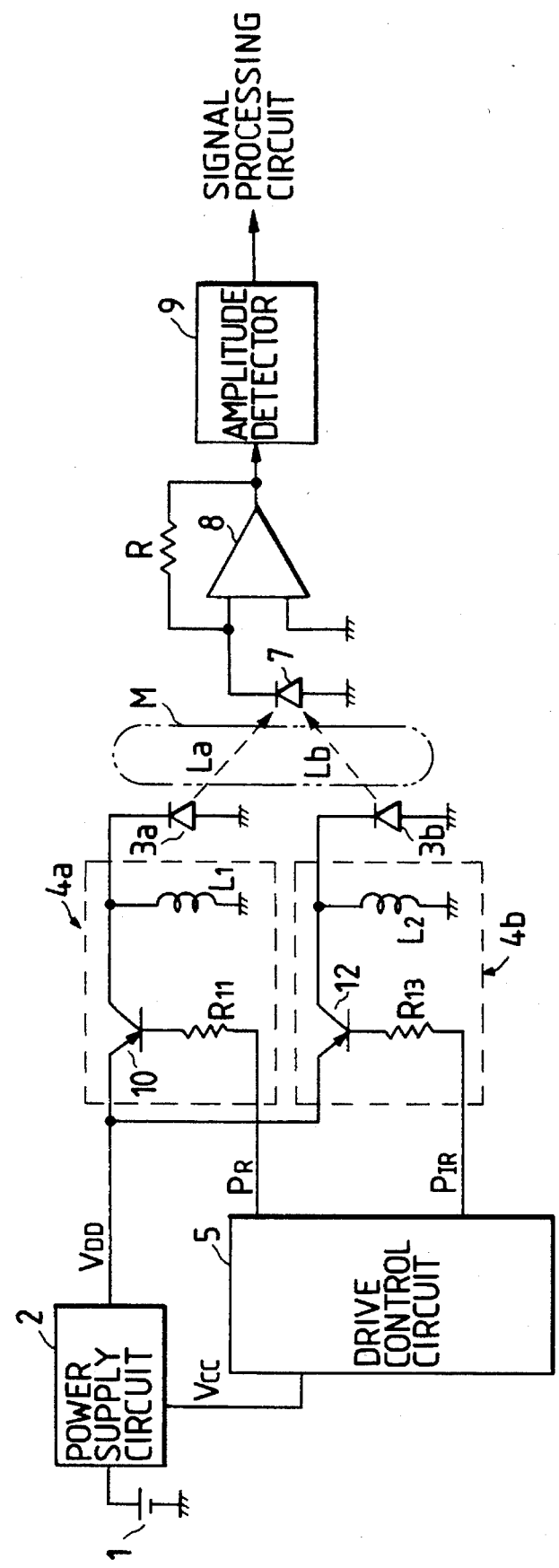
FIG. 1 is a circuit diagram of a pulse oximeter of the present invention using drive circuits for light emitting diodes with the partially block diagram.

FIG. 1 is a block diagram illustrating an overall pulse oximeter using a drive circuit for a light emitting diode according to the present invention with a partly block diagram.

In FIG. 1, the pulse oximeter includes a cell 1 for generating a voltage 1.5 V as a power supply, a power supply circuit 2 for forming stabilized DC power VDD and VCC from the cell 1. A red light emitting element 3a emits a red light, which is driven by a drive circuit described hereinafter, to irradiate a living tissue M of an object.

Further, the pulse oximeter includes an infrared light emitting diode 3b emitting an infrared light, which is driven by a drive circuit described hereinafter, to irradiate the living tissue M of the object, a drive circuit 4a applying the DC power VDD to the red light emitting diode 3a in accordance with a control pulse PR, a drive circuit 4b applying the DC power VDD to the infrared light emitting diode 3b in accordance with a control pulse PIR and a drive control circuit 5 for outputting the control pulses PR and PIR controlled on a time axis to the drive circuit 4a and 4b, respectively.

Furthermore, the pulse oximeter includes a photodiode 7 for generating a photoelectric transfer signal by receiving transmitted light La and Lb (or reflected light) in such a manner that the red and infrared light emitted from the red and infrared emitting diodes 3a and 3b travel through the living tissue M, respectively, an operational amplifier 8 for amplifying the photoelectric transfer signal and an amplitude detector 9 for detecting an amplitude signal outputted from the operational amplifier 8 and for transmitting the amplitude signal to a signal processing circuit (not shown).

Next, a configuration of the driving circuits 4a and 4b will be described hereinafter.

The driving circuit 4a contains a switching transistor 10 that DC power VDD is applied to an emitter of the switching transistor 10, resistor R11 for inputting the control pulse PR generated by the drive control circuit 5 into a base of the switching transistor 10 and an inductor L1 connected in parallel to the red light emitting diode 3a which is connected between the a collector of the switching transistor 10 and a ground.

The arrangement of driving circuit 4b is the same as an arrangement of driving circuit 4a. Namely, the driving circuit 4b contains a switching transistor 12, resistor R13 for inputting the control pulse PIR generated by the drive control circuit 5 into a base of the switching transistor 12 and an inductor L2 connected in parallel to the infrared light emitting diode 3b which is connected between the a collector of the switching transistor 12 and a ground. Besides, the switching transistors 10 and 12, the driving circuits 4a and 4b are capable of employing various kinds of switching elements.

The operation of the drive circuit will be described hereinafter.

The power supply circuit 2 outputs a stabilized direct current $V_{DD}$ into the drive circuits 4a and 4b and a stabilized direct current Vcc into the drive control circuit 5 from the voltage 1.5 V supplied by the cell 1. The base of the switching transistor 10 provided with the drive circuit 4a receives the control pulse PR for determining a light emission timing through a resistor R11.

The red light emitting diode 3a connected to the drive circuit 4a is irradiated in response to the control pulse PR and the infrared light emitting diode 3b connected to the drive circuit 4b is lit in response to the control pulse PIR.

The light emission timing of the red light emitting diode and the infrared light emitting diode will now be described.

FIGS. 2(a)–2(d) is showing a timing chart of the light emission timing of the red and the infrared light emitting diodes in response to the control pulses PR and PIR, respectively. In FIG. 2(a), when the low signal (L) of the control signal RR is applied to the switching transistor 10 the switching transistor 10 turns on, and the inductor L1 is energized. When the high signal (H) of the control signal PR is applied to the switching transistor 10, the switching transistor 10 turns off, and the red light emitting diode 3a is irradiated by the energy stored in the inductor L1 when the switching transistor 10 was on, as shown in FIG. 2(b).

On the other hand, in FIG. 2(c), when the low signal (L) of the control signal PIR is applied to the switching transistor 12, the switching transistor 12 turns on, and the inductor L2 is energized. When the high signal (H) of the control signal PIR is applied to the switching transistor 12, the switching transistor 12 turns off, and the infrared light emitting diode 3b is irradiated by the energy stored in the inductor L2 when the switching transistor 12 was on, as shown in FIG. 2(d).

The operation of the driving circuit 4a and 4b will described hereinafter with more detail.

FIG. 3 is a wave form chart showing a current and an inverse voltage of the control pulse PR (PIR) and the inductor L1(L2), respectively. In the driving circuit 4a (4b), the control pulse PR (or the control pulse PIR) shown in FIG. 3(a) at a low level (L) is inputted into the base of the switching transistor 10 (12) so that the switching transistor turns on. When the switching transistor turns on, the DC power VDD is supplied to the inductor L1 (L2) and the red emitting diode 3a (3b).

At this time, the red emitting diode 3a (3b) is inversely biased so that no current is allowed to flow therethrough. On the other hand, a current i instantly flows through the inductor L1 (L2) and energizes the inductor L1 (L2) as shown in FIG. 3(b). This current i is expressed by a following equation:

$$i = (E/L)t \qquad (3)$$

where E: voltage of DC voltage VDD

L: inductance of the inductor L1 (L2)

When the control pulse PR (or control pulse PIR) is switched from Low ("L") level to a high ("H") level at a point of time $t_0$, the transistor 10 turns off, an inverse electromotive force is generated in the inductor L1 (L2) as shown in FIG. 3(c) and current is supplied to the red light emitting diode 3a (the infrared light emitting diode 3b) from the inductor L1 (L2).

At this time, when a forward voltage causes the red light emitting diode 3a (the infrared light emitting diode 3b) to light up as V0, the red light emitting diode 3a (the infrared light emitting diode 3b) emits light while a voltage resulting from the inverse electromotive force of the inductor L1 (L2) holds −V0 and maintains this luminous state. The current at the time of light emission increases at a constant ratio of inclination di/dt=V0/L Now, if current io at t=t0 is increased by n times, the average power consumption of the red light emitting diode 3a (the infrared light emitting diode 3b) is increased by $n^2$ times. The current io is determined by a period T that the switching transistor 10 (12) is held ON, the voltage E and the inductance L. Assuming that the E representing the DC power VDD and the L representing the inductance of the inductor L1 (L2) are constant, the current io is determined by the period that the switching transistor 10 (12) is held ON. Under the this condition, a quantity of the light emitted by the red light emitting diode 3a (the infrared light emitting diode 3b) is controllable by causing the drive control circuit 5 to control the ON time of the switching transistor 10 (12). Also, the quantity of light is controllable by controlling the voltage E or the inductance L.

Even when the supply voltage E is not more than the voltage Vo in a forward direction for driving the red light emitting diode 3a (the infrared light emitting diode 3b), the red light emitting diode 3a (the infrared light emitting diode 3b) could be lit by lengthening the ON time T of the switching transistor 10.

If a power loss of the switching transistor 10 is rather small, a power utilization efficiency may be closer to 100% on the condition that the power loss is almost nearly zero. The controlled variable of the current flowing through the red light emitting diode 3a may be determined on the basis of the quantity of light received on the photodiode 7 or a detected voltage as a voltage existing across a detection resistor inserted between the photodiode 7 and the ground.

More specifically, the red light emitting diode 3a (the infrared light emitting diode 3b) is lit with a period of 1.6 msec at light emission duty ratio of 25% when the cell 1 was set at 1.5 V and when the inductor L1 at 3.3 mH was employed. At this time, 80 mA of peak current io flowed through the red light emitting diode 3a (the infrared light emitting diode 3b).

The operation of the drive circuits 4a and 4b is described above.

In this operation, the red light La of the red light emitting diode 3a and the infrared light Lb of the infrared light emitting diode 3b are alternatively irradiated to the living tissue M so that the transmitted light or the reflected light are received alternatively by the photodiode 7. The photodiode 7 generates the photoelectric transfer signal which is amplified by the operational amplifier 8. After that, the photoelectric transfer signal is detected by the amplitude defecter 9 to obtain amplification value indicating the light absorption of the red light La or the infrared light Lb. The light absorption of the red light and the infrared light are inputted into the signal processing circuit (not shown). At the signal processing circuit, the ratio φ between the light absorption of the two different wavelengths are calculated by the equations (1) and (2) described above. Afterwards, the degree S of the oxygen saturation is determined in view of the value of ratio φ.

Another arrangement of the drive circuit 4a and 4b of the present invention are described hereinafter.

In FIG. 1, the drive circuits 4a and 4b and the control pulses PR and PIR generated by the drive control circuit 5 intermittently apply the inverse bias voltage to the red light emitting diode 3a and the infrared light emitting diode 3b. Instead of utilizing the switching transistors 10 and 12, the drive circuits are capable of employing electromagnetic switches.

Figure 4:
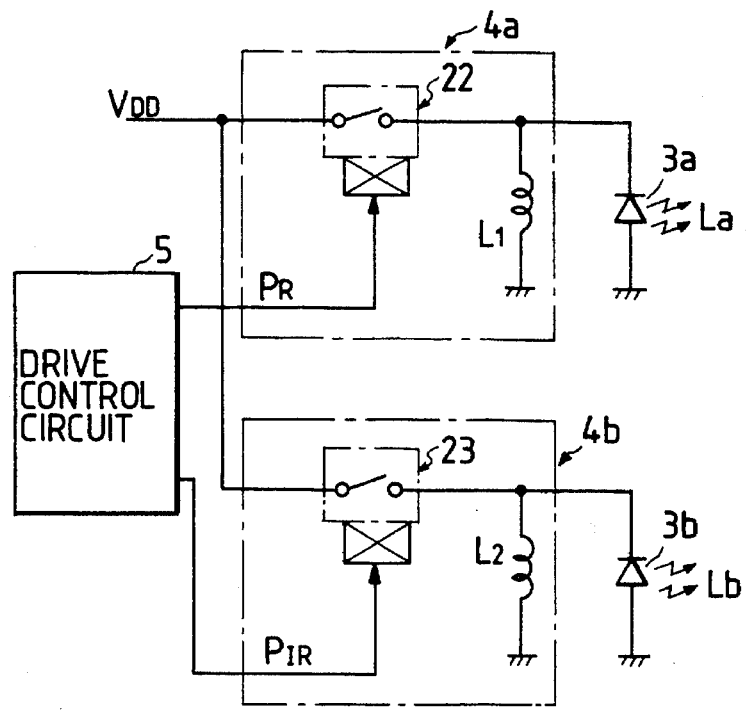
FIG. 4 is a circuit diagram of a driving circuit of the present invention containing an electromagnetic switch.

FIG. 4 is a showing a circuit diagram of the drive circuits employing electromagnetic switches. In these drive circuits 4a and 4b, under the condition that an ON/Off switching speed (ON/OFF) is in rather slow, the electromagnetic switches 22 and 23 turning on/off in response to the control pulses PR and PIR are employed instead of the switching transistors 10 and 12. The ON/Off switching operation of the electromagnetic switches 22 and 23 and the light emission timing of the red light emitting diode 3a and the infrared light emitting diode 3b are the same as the timing chart shown in FIG. 2. The other arrangement of this drive circuit is the same as the arrangement shown in FIG. 1.

Figure 5:
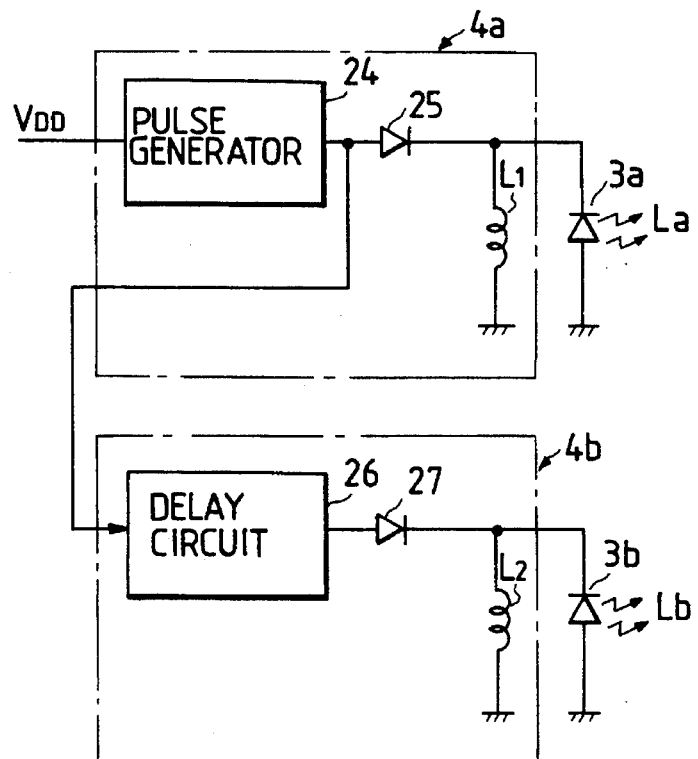
FIG. 5 is a circuit diagram of a driving circuit of the present invention containing a pulse generator.

In FIG. 5, the pulse generator 24 is employed instead of the drive control circuit 5 and the switching transistors 10 and 12 which are used for switching ON/Off states of the DC power VDD. A pulse generated by the pulse generator 24 is applied to the red light emitting diode 3a through the diode 25 for prevention of a reverse current. Moreover, the pulse generated by the pulse generator 24 is delayed by the delay circuit 26. A delayed pulse is supplied to the red light emitting diode through the diode 27.

The other configuration are the same as that shown in FIG. 1, and the arrangement of the pulse generated by the pulse generator 24 and the delayed pulse outputted by the delay circuit 26 in the time axis and the light emission timing of the red light emitting diode 3a and the infrared light emitting diode 3b are the same as the timing chart shown in FIG. 2. In this configuration, the switching transistors 10 and 12, and the drive control circuit 5 for controlling the switching transistors 10 and 12 by the control pulse PR and PIR are. omitted from the configuration shown in FIG. 1 so as to simplify the configuration of the drive circuit.

Figure 6:
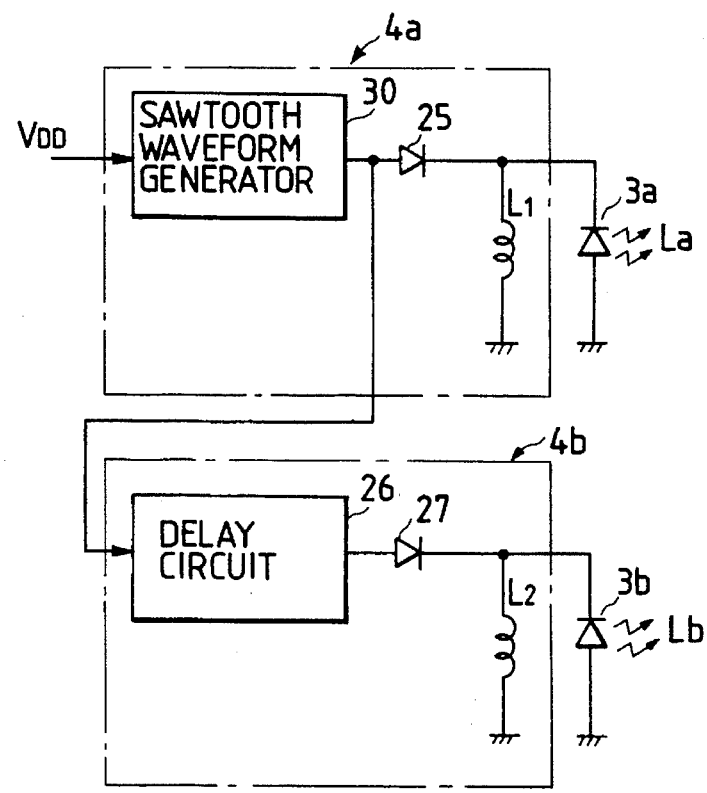
FIG. 6 is a circuit diagram of a driving circuit of the present invention containing a sawtooth waveform generator.

FIG. 6 is a circuit diagram of the drive circuit employing a sawtooth waveform generator 30 instead of the pulse generator 24 shown in FIG. 5. The sawtooth waveform generator 30 generates a sawtooth wave in the shape that the voltage is gradually increased and the voltage is rapidly shifted from a maximum voltage. The sawtooth wave is applied to the red light emitting diode 3a through the diode 25 for prevention of inverse current. Moreover, the sawtooth wave generated by the sawtooth waveform generator 30 is delayed by the delay circuit 26 to obtain a delayed sawtooth wave which is supplied to the infrared light emitting diode 3b through the diode 27.

The other configurations of this drive circuit are the same as that of FIG. 1 and the arrangement of the sawtooth wave generated by the sawtooth waveform generator 30 and the delayed sawtooth wave outputted by the delay circuit 26 in the time axis and the light emission timing of the red light emitting diode 3a and the infrared light emitting diode 3b are the same as the timing chart shown in FIGS. 2(a)–2(d).

In this configuration, the switching transistors 10 and 12 and the drive control circuit 5 for controlling the switching transistor 10 and 12 by the control pulse PR and PIR are omitted so as to simplify the configuration of the drive circuit.

Moreover, this configuration leads the prevention of applying an overvoltage to the red light emitting diode 3a (the infrared light emitting diode 3b). Namely, when the pulse is applied, the overvoltage instantaneously existing in the inductor L1 (the inductor L2) at the rasing portion of the pulse waveform (going edge) is applied to the red light emitting diode 3a (the infrared light emitting diode 3b). On the other hand, when the sawtooth wave is applied to the inductor L1 (L2) or the red light emitting diode 3a (3b), the red light emitting diode 3a (the infrared light emitting diode 3b) is protected, because the instantaneous overvoltage does not occur when the voltage of the sawtooth wave is gradually increased.

Figure 7:
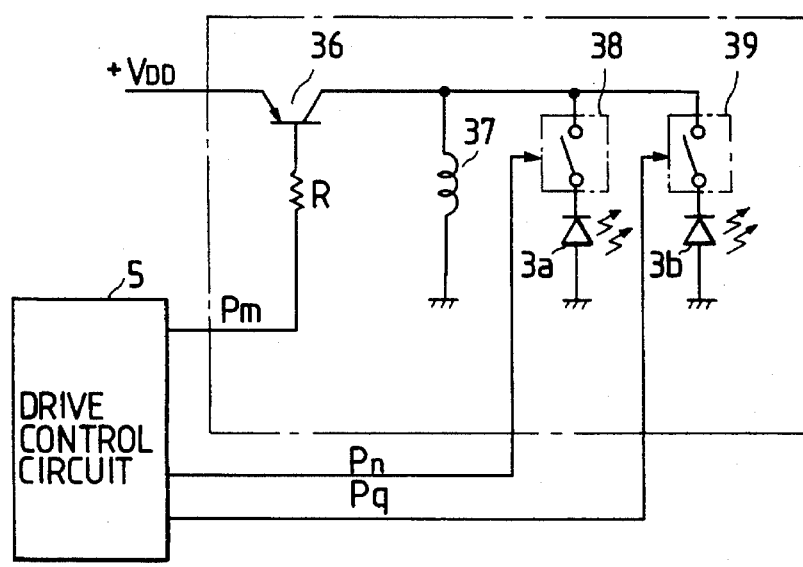
FIG. 7 is a circuit diagram of a driving circuit of the present invention containing a common inductor.

FIG. 7 is a showing a circuit diagram of the drive circuit which employs a common inductor 37. In FIG. 7, the drive circuit contains a switching transistor 36 turning on and off in response to a control pulse Pm transmitted by the drive control circuit 5. Moreover, the drive circuit further contains a inductor 37 connected between the collector of the switching transistor 36 and the ground, the red light emitting diode 3a connected to the inductor 37 in parallel, a switch 38, which turns on when a control pulse Pn is received, connected to the collector of the switching transistor 36 in serious, the infrared light emitting diode 3b connected to the inductor 37 in parallel and a switch 39, which turns on when a control pulse Pq is received, connected to the infrared light emitting diode 3b in serious.

In this configuration, the switching transistor 36 turns on when the control pulse Pm is transmitted from the drive control circuit 5. Energy is stored in the inductor 37 when the switching transistor 36 is held On, and the energy of the inductor 37 is supplied to the red light emitting diode 3a through the switch 38, and the red light emitting diode emits red light. The switch 38 is turned on by receiving the control pulse Pn generated by the drive control circuit 5. After emitting the red light, the switching transistor 36 turns on when the control pulse Pm generated by the drive control circuit 5 is applied thereto. Energy is stored in the inductor 37 when the switching transistor 36 is held ON. The energy of the inductor 37 is supplied to the infrared light emitting diode 3b through the switch 39 in order to emit the infrared light. The switch 39 is turned on by receiving the control pulse Pn generated by the drive control signal 5.

In this drive circuit, a positive power supply+VDD is used as the DC power supply. However, it is possible of employing a negative power supply−VDD in view of the circuit configuration. In this case, as used in the negative power supply, it is necessary to use red and the infrared light emitting diodes with polarity opposite to the embodiment described above, and a pnp type switching transistor is used instead of the npn type switching transistor 36 as shown in FIG. 7.

The present invention is not limited by these embodiments described above. It is possible to modify the configuration without diverting the scope of the present invention. Namely, an object of the present invention is to provide the power supply which intermittently applies the voltage to the inductor connected the two light emitting diode in parallel.

As described above, the drive circuit for a light emitting diode in a pulse oximeter of the present invention, the light emitting elements are irradiated by utilizing the inverse electromotive voltage so as to employ the relative low voltage cell without sacrificing the S/N ratio so that the current consumption is increased. Moreover, two light emitting diodes different in wavelength are alternatively irradiated by utilizing the inverse voltage of one inductor so that two light emitting diodes are irradiated by utilizing the inverse voltage of one inductor on the time sharing basis under the condition that the voltage is not more than the light emission starting voltage the light emitting diode so as to simplify the circuit thereof.

Therefore, a pulse oximeter will be easily developed with utilizing the relatively low voltage supply such as the cell to carry the pulse oximeter with long time measurement.

What is claimed is:

1. A drive circuit for use in a pulse oximeter for measuring a degree of oxygen saturation of arterial blood in a living tissue, said drive circuit comprising:

at least two light emitting elements different in wavelength for irradiating said living tissue containing said arterial blood;

a light receiving element for receiving light irradiated from said light emitting elements and traversing said living tissue directly and indirectly to said light receiving element;

means for intermittently applying an inverse bias voltage across said light emitting elements;

means including at least one inductor for applying an inverse electromotive voltage across said light emitting elements, said means for applying an inverse electromotive voltage being connected to said light emitting elements and to said means for intermittently applying an inverse bias voltage; and signal processing means which is capable of calculating a ratio of a change of light absorption of at least two wavelengths transmitted alternatively from said light emitting elements, wherein said ratio is based on signals output from said light receiving element and said ratio represents said degree of oxygen saturation of said arterial blood.

2. A drive circuit for use in a pulse oximeter as claimed in claim 1, wherein said means for applying an inverse bias voltage comprises:

one inductor which is connected in parallel to all of said light emitting elements, wherein a DC voltage supplied by said power supply creates said inverse electromotive voltage within said inductor which in turn applies an inverse bias voltage across said light emitting elements; and a drive control circuit, wherein said drive control circuit outputs at least one light element control pulse to control the application of said inverse bias voltage across said light emitting elements, such that said inverse bias voltage is alternatively applied to each of said light emitting elements.

3. A drive circuit for use in a pulse oximeter as claimed in claim 2, wherein said means for applying an inverse bias voltage further comprises:

a switching means which comprises a plurality of switching devices;

a first input of each of said switching devices which is connected to said inductor and inputs said inverse bias voltage created by said inverse electromotive force of said inductor;

a first output of each of said switching devices which is connected to at least one of said light emitting elements; and a second input of each of said switching devices, which is connected to said drive control circuit, wherein said drive control circuit intermittently outputs at least one of said light element control pulses to said second input of at least one of said switching devices in order to alternatively apply said inverse bias voltage to each of said light emitting elements.

4. A drive circuit for use in a pulse oximeter as claimed in claim 3, wherein at least one of said switching devices is an electrical switch.

5. A drive circuit for use in a pulse oximeter as claimed in claim 3, wherein at least one of said switching devices is a transistor.

6. A drive circuit for use in a pulse oximeter as claimed in claim 3, wherein said means for applying an inverse bias voltage further comprises:

an enabling means for controlling an application of said DC voltage output from said power supply to said inductor.

7. A drive circuit for use in a pulse oximeter as claimed in claim 6, wherein said enabling means comprises:

a transistor;

an emitter of said transistor which is electrically connected to said power supply;

a collector of said transistor which is electrically connected to said inductor and said switching means; and a base of said transistor which inputs an enabling means control signal which is output from said drive control circuit to said enabling means in order to control the application of DC voltage output from said power supply to said inductor.

8. A drive circuit for use in a pulse oximeter as claimed in claim 7, wherein at least one of said light emitting elements emits a red light and at least another of said light emitting elements emits an infrared light.

9. A drive circuit for use in a pulse oximeter as claimed in claim 6, wherein said means for applying an inverse bias voltage produces:

an enabling means control signal which is output from said drive control circuit to said enabling means in order to control the application of said DC voltage output from said power supply to said inductor.

10. A drive circuit for use in a pulse oximeter as claimed in claim 9, wherein said enabling means is an electrical switch.

11. A drive circuit for use in a pulse oximeter as claimed in claim 10, wherein at least one of said light emitting elements emits a red light and at least another of said light emitting elements emits an infrared light.

12. A drive circuit for driving a light emitting diode in a pulse oximeter as claimed in claim 1, wherein said means for applying an inverse electromotive voltage comprises:

a plurality of inductors, wherein each of said inductors is connected in parallel to at least one of said light emitting elements.

13. A drive circuit for driving a light emitting diode in a pulse oximeter as claimed in claim 12, wherein said means for intermittently applying an inverse bias voltage comprises:

power supply means for outputting a first DC voltage;

switching means, which inputs said first DC voltage from said power supply means, for applying said first DC voltage to each of said inductors in an alternative application.

14. A drive circuit for driving a light emitting diode in a pulse oximeter as claimed in claim 13, wherein said means for intermittently applying an inverse bias voltage further comprises:

a drive control circuit, wherein said drive control circuit inputs a second DC voltage output from said power supply means and wherein said drive control circuit outputs at least one light element control pulse to said switching means for controlling said alternative application of said first DC voltage to each of said inductors.

15. A drive circuit for driving a light emitting diode in a pulse oximeter as claimed in claim 14, wherein said switching means comprises:

a plurality of switching devices;

a first terminal of each of said switching devices which is connected to at least one of said inductors and to at least one of said light emitting elements;

a second terminal of each of said switching devices which is connected to said power supply means and inputs said first DC voltage from said power supply means; and a third terminal of each of said switching devices which inputs at least one of said light element control pulses from said drive control circuit.

16. A drive circuit for driving a light emitting diode in a pulse oximeter as claimed in claim 15, wherein at least one of said switching devices is a transistor, said first terminal is a collector, said second terminal is an emitter, and said third terminal is a base.

17. A drive circuit for driving a light emitting diode in a pulse oximeter as claimed in claim 16, wherein at least one of said light emitting elements is a red light emitting element and at least another of said light emitting elements is an infrared light emitting element.

18. A drive circuit for use in a pulse oximeter as claimed in claim 15, wherein at least one of said switching devices an electrical switch.

19. A drive circuit for use in a pulse oximeter as claimed in claim 18, wherein at least one of said light emitting elements emits a red light and at least another of said light emitting elements emits an infrared light.

20. A drive circuit as claimed in claim 14, wherein said first DC voltage and said second DC voltage are different DC voltages.

21. A drive circuit for use in a pulse oximeter as claimed in claim 12, wherein said means for applying an inverse bias voltage further comprises:

a voltage generating means for altering a DC voltage output from said power supply; and a first diode that has an input which is connected to an output of said voltage generating means and an output which is connected to at least one of said inductors, wherein said first diode controls a directional flow of said output of said voltage generating means.

22. A drive circuit for use in a pulse oximeter as claimed in claim 21, wherein said means for applying an inverse bias voltage further comprises:

a delay circuit means which is connected to said output of said voltage generating means in order to delay said output of said voltage generating means in a manner such that said output of said voltage generating means is alternatively applied across each of said inductors; and a second diode that has an input which is electrically connected to an output of said delay circuit means and an output which is connected to at least one of said inductors, wherein said second diode controls a directional flow of said output of said delay circuit means.

23. A drive circuit for use in a pulse oximeter as claimed in claim 21, wherein said output of said voltage generating means creates said inverse electromotive voltage within at least one of said inductors which in turn applies a inverse bias voltage across at least one of said lighting elements.

24. A drive circuit for use in a pulse oximeter as claimed in claim 22, wherein said output of said delay circuit means creates said inverse electromotive voltage within at least one of said inductors which in turn applies a inverse bias voltage across at least one of said lighting elements.

25. A drive circuit for use in a pulse oximeter as claimed in claim 24, wherein said output of said voltage generating means creates said inverse electromotive voltage within at least one of said inductors which in turn applies a inverse bias voltage across at least one of said lighting elements.

26. A drive circuit for use in a pulse oximeter as claimed in claim 25, wherein said voltage generating means is a pulse generator.

27. A drive circuit for use in a pulse oximeter as claimed in claim 26, wherein at least one of said light emitting elements emits a red light and at least another of said light emitting elements emits an infrared light.

28. A drive circuit for use in a pulse oximeter as claimed in claim 25, wherein said voltage generating means a sawtooth waveform generator.

29. A drive circuit for use in a pulse oximeter as claimed in claim 28, wherein at least one of said light emitting elements emits a red light and at least another of said light emitting elements emits an infrared light.

30. A drive circuit as claimed in claim 1, wherein said means for applying an inverse electromotive voltage comprises:

inductance means for receiving a DC voltage from said means for intermittently applying an inverse bias voltage, generating an inverse electromotive force according to said DC voltage, and applying said inverse electromotive voltage across at least one of said light emitting elements in response to said inverse electromotive force.

31. A drive circuit as defined in claim 1, further comprising saturation calculating means for measuring a degree of oxygen saturation of arterial blood based on an output of said signal processing means.

* * * * *